United States Patent

Hickey et al.

[11] Patent Number: 5,981,789
[45] Date of Patent: Nov. 9, 1999

[54] PREPARATION OF NUCLEAR CHLORINATED AROMATIC COMPOUNDS

[75] Inventors: John Hickey, Grand Island; Robert L. Bell, Amherst; George Piotrowski, Cheektowaga, all of N.Y.

[73] Assignee: Occidental Chemical Corporation, Dallas, Tex.

[21] Appl. No.: 09/223,709

[22] Filed: Dec. 30, 1998

[51] Int. Cl.⁶ .................. C07C 255/00; C07C 263/00; C07C 51/58; C07C 41/00
[52] U.S. Cl. .................. 558/425; 560/358; 562/840; 568/656; 570/127; 570/185; 570/251
[58] Field of Search .................. 558/425; 560/358; 562/840; 568/656; 570/127, 185, 251

[56] References Cited

U.S. PATENT DOCUMENTS 4,582,948  4/1986  Tang et al. .................. 568/938

*Primary Examiner*—Johann Richter
*Assistant Examiner*—Joseph Murray
*Attorney, Agent, or Firm*—Anne E. Brookes; Richard D. Fuerle

[57] ABSTRACT

Disclosed is a method of preparing an aromatic compound having the general formula

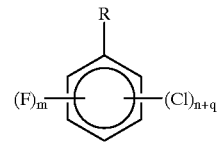

where R is $CF_3$, $OCF_3$, $OC_2F_5$, CN, NCO, or COCl, m is 0, 1, or 2, n is 0, 1, or 2, q is 1 or 2, and q+m+n is an integer from 1 to 5. A vapor is prepared of a substrate having the general formula

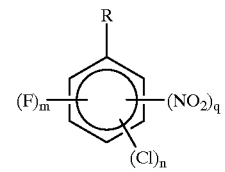

and a chlorinating agent. The mixture is reacted at a temperature above the boiling point of the substrate but below its decomposition temperature. The amount of chlorinating agent is about 0.5 to about 2 times the amount stoichiometrically required to replace the nitro groups on the substrate with chlorine. Unreacted substrate and partially reacted substrate are condensed from the product mixture and are recycled. The substrate is preferably in contact with the chlorinating agent before it is vaporized.

20 Claims, No Drawings

PREPARATION OF NUCLEAR CHLORINATED AROMATIC COMPOUNDS

BACKGROUND OF THE INVENTION

This invention relates to a process for chlorodenitrating aromatic compounds. In particular, it relates to chlorodenitrating aromatic compounds using less chlorinating agent and lower temperatures, then recycling the product mixture to increase the yield.

U.S. Pat. Nos. 4,470,930 and 4,582,948 describe a process for the nuclear chlorination of aromatic compounds. In that process, an aromatic compound having nitro and other groups on the ring is heated in the presence of a chlorinating agent, which results in the replacement of the nitro groups by chlorine. To obtain a high yield, excess chlorine and higher temperatures are used.

While the yield in the process described in those patents is good, the product also contains partially chlorinated intermediates, unreacted starting material, and overchlorinated byproducts. Separation of the desired product from these undesirable byproducts and unreacted starting material by distillation can result in the decomposition of the partially chlorinated intermediates and the unreacted starting material.

SUMMARY OF THE INVENTION

We have found that the process described in U.S. Pat. Nos. 4,470,930 and 4,582,948 can be improved upon by using very little excess chlorine, or even less than a stoichiometric amount of chlorine, and by heating at relatively low temperatures. While this initially results in a significantly lower yield of the desired product, the product mixture contains very little overchlorinated byproduct. We have found that by condensing the unreacted starting material and the partially chlorinated starting material from the product mixture and repeatedly recycling them, the final product can be made in very high yield while, at the same time, significant quantities of overchlorinated compounds are not produced.

DESCRIPTION OF THE PREFERRED EMBODIMENTS

The substrate for the process of this invention has the general formula

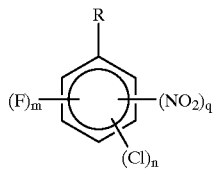

where R is $CF_3$, $OCF_3$, $OC_2F_5$, CN, NCO, or COCl, m is 0, 1, or 2, n is 0, 1, or 2, q is 1 or 2, and q+m+n is an integer from 1 to 5. In this formula, R is preferably $CF_3$, m is preferably 0, n is preferably 1, and q is preferably 2 as those compounds are more important commercially. The preferred starting material is 4-chloro-3,5-dinitrobenzotrifluoride (CDN-BTF), as the product formed by the chlorodenitration of this substrate, 3,4,5-trichlorobenzotrifluoride, is used to make an agricultural intermediate for making a herbicide.

Chlorinating agents that can be used for the process of this invention include chlorine gas, hydrogen chloride gas, thionyl chloride, sulfuryl chloride, sulfur chloride, phosgene, and phosphorous trichloride. However, the preferred chlorinating agent is chlorine gas as it is inexpensive and reacts well. The amount of chlorinating agent should be carefully controlled. About 0.5 to about 2 times the amount of chlorinating agent required to stoichiometrically replace the nitro groups on the aromatic compound should be used. If less than 0.5 times as much chlorinating agent is used, too much recycling will be required to bring the yield to high levels, and if more than 2 times the amount of chlorinating agent needed is used, more overchlorinated byproducts will be produced. The preferred amount of chlorinating agent is about 0.8 to about 1.4 times the amount stoichiometrically required.

The chlorodenitration reaction is performed in the vapor phase, which requires the vaporization of the substrate. Typically, the substrate is a low melting point solid which is melted and charged into a vaporizer where it is heated to its boiling point. It is preferable to add the chlorinating agent before the substrate is vaporized because if the substrate is vaporized in the absence of the chlorinating agent it may decompose. Decomposed substrate does not react with the chlorinating agent and is therefore wasted.

The vaporized reactants are preferably reacted in a vapor phase reactor that is separate from the vaporizer. It is preferable to use a packed column for this reactor as that facilitates heat and mass transfer and mixing of the reactants. The column can be packed with an inert material such as nickel metal, stainless steel, or various ceramics. It is preferable to use a conductive packing material, such as a metal, for better heat transfer. Since the typical residence time in the vapor phase reactor is about a minute or two, the reactor volume should be selected to accommodate the volume of reactants.

The reaction temperature is above the boiling point of the substrate but below its decomposition temperature. A preferred temperature range is about 290 to about 350° C. At lower temperatures too little product is produced and at higher temperatures more overchlorinated byproduct is produced. For example, if the substrate is CDN-BTF, higher temperatures can result in the production of 2,3,4,5-tetrachlorobenzotrifluoride or even products such as 1,2,3,4,5-pentachlorobenzene or hexachlorobenzene. No catalyst is needed in this reaction.

The desired product has the general formula:

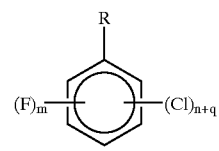

where R, m, n, and q were hereinabove defined.

Examples of chloro-substituted benzotrifluorides that can be made by the process of this invention include 2-chlorobenzotrifluoride; 3-chlorobenzotrifluoride; 4-chlorobenzotrifluoride; 3-chloro-4-fluorobenzotrifluoride; 4-chloro-3-fluorobenzotrifluoride; 2-chloro-5-fluorobenzotrifluoride; 5-chloro-2-fluorobenzotrifluoride; 2-chloro4-fluorobenzotrifluoride; 4-chloro-2-fluorobenzotrifluoride; 3-chloro-5-fluorobenzotrifluoride; 2,5-dichloro-4-fluorobenzotrifluoride; 4,5-dichloro-2-fluorobenzotrifluoride; 3,5-dichloro-4-fluorobenzotrifluoride; 3,4-difluoro-5-chlorobenzotrifluoride; 2,5-difluoro-3-chlorobenzotrifluoride; 3,5-difluoro-4-chlorobenzotrifluoride; and 3,4-5-trichlorobenzotrifluoride.

Examples of chloro-substituted benzoyl chlorides that can be prepared include 2-chlorobenzoyl chloride; 3-chlorobenzoyl chloride; 4-chlorobenzoyl chloride; 4-chloro-3-fluorobenzoyl chloride; 3-chloro4-fluorobenzoyl chloride; 2-chloro-4-fluorobenzoyl chloride; 4-chloro-2-fluorobenzoyl chloride; 2-chloro-5-fluorobenzoyl chloride; 5-chloro-2-fluorobenzoyl chloride; 3-chloro-5-fluorobenzoyl chloride; 2,5-dichloro-4-fluorobenzoyl chloride; 3,5-dichloro-4-fluorobenzoyl chloride; 4,5-dichloro-2-fluorobenzoyl chloride; 3,4-difluoro-5-chlorobenzoyl chloride; 3,5-difluoro-4-chlorobenzoyl chloride; and 3,4,5-trichlorobenzoyl chloride.

Examples of chloro-substituted trifluoromethoxybenzenes that can be prepared include 2-chlorotrifluoromethoxybenzene; 3-chlorotrifluoromethoxybenzene; 4-chlorotrifluoromethoxy benzene; 3-chloro-4-fluorotrifluoromethoxybenzene; 2-chloro4-fluorotrifluoromethoxybenzene; 4-chloro-2-fluorotrifluoromethoxybenzene; 2-chloro-5-fluorotrifluoromethoxybenzene; 5-chloro-2-fluorotrifluoromethoxybenzene; 3-chloro-5-fluorotrifluoromethoxybenzene; 2,5-dichloro-4-fluorotrifluoromethoxybenzene; 4,5-dichloro-2-fluorotrifluoromethoxybenzene; 3,5-dichloro-4-fluoromethoxybenzene; 3,4-difluoro-5-chlorotrifluoromethoxybenzene; 2,5-difluoro-3-chlorotrifluoromethoxybenzene; 3,5-difluoro-4-chlorotrifluoromethoxybenzene; and 3,4,5-trichlorotrifluoromethoxybenzene.

Examples of chloro-substituted pentafluoroethoxybenzenes that can be prepared include 2-chloropentafluoroethoxybenzene; 3-chloropentafluoroethoxybenzene; 4-chloropentafluoroethoxybenzene; 2-chloro-5-fluoropentafluoroethoxybenzene; 5-chloro-2-fluoropentafluoroethoxybenzene; 3-chloro-4-fluoropentafluoroethoxybenzene; 4-chloro-3-fluoropentafluoroethoxybenzene; 2-chloro-4-fluoropentafluoroethoxybenzene; 4-chloro-2-fluoropentafluoroethoxybenzene; 3-chloro-5-fluoropentafluoroethoxybenzene; 2,5-dichloro-4-fluoropentafluoroethoxybenzene; 4,5-dichloro-2-fluoropentafluoroethoxybenzene; 3,5-dichloro-4-fluoropentafluoroethoxybenzene; 3,4-difluoro-5-chloropentafluoroethoxybenzene; 2,5-difluoro-3-chloropentafluoroethoxybenzene; 3,5-difluoro-4-chloropentafluoroethoxybenzene; and 3,4,5-trichloropentafluoroethoxybenzene.

Examples of chloro-substituted benzonitriles that can be prepared include 2-chlorobenzonitrile; 3-chlorobenzonitrile; 4-chlorobenzonitrile; 2-chloro,-5-fluorobenzonitrile; 5-chloro-2-fluorobenzonitrile; 3-chloro-4-fluorobenzonitrile; 4-chloro-3-fluorobenzonitrile; 2-chloro-4-fluorobenzonitrile; 4-chloro-2-fluorobenzonitrile; 3-chloro-5-fluorobenzonitrile; 2,5-dichloro-4-fluorobetnzonitrile; 4,5-dichloro-2-fluorobenzonitrile; 3,5-dichloro-4-fluorobenzonitrile; 3,4-difluoro-5-chlorobenzonitrile; 2,5-difluoro-3-chlorobenzonitrile; 3,5-difluoro-4-chlorobenzonitrile; and 3,4,5-trichlorobenzonitrile.

Examples of chloro-substituted phenyl isocyanates that may be prepared are 2-chlorophenyl isocyanate; 3-chlorophenyl isocyanate; 4-chlorophenyl isocyanate; 2-chloro-5-fluorophenyl isocyanate; 5-chloro-2-fluorophenyl isocyanate; 3-chloro-4-fluorophenyl isocyanate; 4-chloro-3-fluopheryl isocyanate; 2-chloro4-fluorophenyl isocyanate; 4-chloro-2-fluoropheryl isocyanate; 3-chloro-5-fluorophenyl isocyanate; 2,5-dichloro-4-fluororpheyl isocyanate; 4,5-dichloro-2-fluorophenyl isocyanate; 3,5-dichloro-4-fluorophenyl isocyanate; 3,4-difluoro-5-chlorophenyl isocyanate; 2,5-difluoro-3-chlorophenyl isocyanate; 3,5-difluoro-4-chlorophenyl isocyanate; and 3,4,5-trichlorophenyl isocyanate.

The product mixture contains the desired product as well as unreacted substrate, partially reacted substrate, and a small amount of overchlorinated byproduct. The product mixture is sent to a partial condenser where aromatics that boil below the boiling point of the desired product are condensed. The partial condenser is preferably another heated column packed in the same manner as the reactor. Normally, the desired product will be the highest boiling aromatic. For example, if the desired product is 3,4,5-trichlorobenzotrifluoride, the condenser temperature is set at about 180 to about 200° C. so that the desired product does not condense but CDN-BTF, 3,4-dichloro-5-nitrobenzotrifluoride, 4,5-dichloro-3-nitrobenzotrifluoride, and overchlorinated byproducts do condense. The temperature of the partial condenser should be selected so that the substrate, partially reacted substrate, and possibly even part of the product are condensed, with the result that at least 95 wt % of the organic overhead from the partial condenser is the desired product. Preferably, the temperature of the partial condenser is selected so that at least 99 wt % of its organic overhead is the desired product. These condensed materials are then recycled to the vaporizer. Since any overchlorinated byproduct that is present will also be recycled with the substrate and partially reacted substrate, its concentration will eventually build up in the recycling loop. Overchlorinated byproducts can be removed from the system periodically by, for example, filtration or other means.

The desired product can be recovered from the partial condenser overhead by condensation. The chlorine and nitrogen dioxide gases that are present can be scrubbed with water or caustic or they can be treated by other means.

The following examples further illustrates this invention.

EXAMPLE 1

Chlorine and CDN-BTF were continuously charged to a 1-inch (2.54 cm) tubular nickel reactor consisting of an unpacked vaporizer section, a reactor section packed with nickel mesh, and a partial condenser section also packed with nickel mesh. The chlorine (120 cc/min) and the CDN-BTF (1.46 g/min) were mixed, then fed into the vaporizer. The molar ratio of chlorine to CDN-BTF was 0.98.

The vaporizer was heated to 315 to 320° C. to totally vaporize the CDN-BTF. The mixed CDN-BTF and chlorine were fed to the packed reactor section, which was heated to 330° C. The reactor section was sized to allow a residence time for the chlorine/CDN-BTF mixture of 1 to 2 minutes.

The resulting vapor reaction product mixture was fed to the partial condenser section, which was heated to 190° C., where unreacted CDN-BTF, reaction intermediate, and a portion of the desired product, 3,4,5-trichlorobenzotrifluoride, were condensed and collected.

The remaining vapor, containing unreacted chlorine, nitrogen dioxide, 3,4,5-trichlorobenzotrifluoride, and a small amount of reaction intermediate, was vented to a condenser, where the organic compounds were condensed and collected and the chlorine and nitrogen dioxide were scrubbed. The 3,4,5-trichlorobenzotrifluoride collected was 97% pure.

The isolated yield of 3,4,5-trichlorobenzotrifluoride was 68%. When the recovered starting material, reaction intermediate, and product collected from the partial condenser were recycled, the yield increased to 96%.

EXAMPLE 2—COMPARATIVE

Example 1 was repeated except that no partial condenser was used. The 3,4,5-trichlorobenzotrifluoride collected was 75% pure. The isolated yield of 3,4,5-trichlorobenzotrifluoride was 78%. Distillation of the material to a higher purity was undesirable because the high concentration of high boiling nitro- and dinitro- compounds present would concentrate in the distillation bottoms.

EXAMPLE 3—COMPARATIVE

Example 2 was repeated except that the CDN-BTF was fed to the vaporizer and the chlorine was added to the vaporized CDN-BTF prior to introduction into the reactor section. The 3,4,5-trichlorobenzotrifluoride collected was 75% pure. The isolated yield of 3,4,5-trichlorobenzotrifluoride was 67%. Distillation of the material to a higher purity was undesirable because the high concentration of high boiling nitro- and dinitro- compounds present would concentrate in the distillation bottoms. Inspection of the condenser after the reaction revealed that approximately 10% of the CDN-BTF charged had decomposed in the vaporizer and had deposited on the walls of the vaporizer.

We claim:

1. A method of making a chlorinated aromatic compound having the general formula

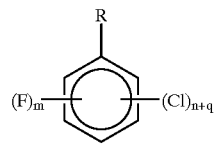

comprising
   (A) preparing a vaporized mixture of a chlorinating agent and a substrate having the general formula

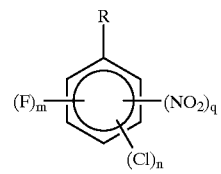

where R is $CF_3$, $OCF_3$, $OC_2F_5$, CN, NCO, or COCl, m is 0, 1, or 2, n is 0, 1, or 2, q is 1 or 2, q+m+n is an integer from 1 to 5, and the amount of chlorinating agent in said mixture is about 0.5 to about 2 times the amount stoichiometrically required to replace the nitro groups on said substrate with chlorine;
   (B) heating said vaporized mixture to a temperature above the boiling point of said substrate but below its decomposition temperature to produce a product mixture;
   (C) condensing said substrate and partially reacted substrate from said product mixture; and
   (D) recycling said condensed substrate and said condensed partially reacted substrate to step (A).

2. A method according to claim 1 wherein R is $CF_3$.
3. A method according to claim 1 wherein m is 0.
4. A method according to claim 1 wherein n is 1.
5. A method according to claim 1 wherein q is 2.
6. A method according to claim 1 wherein said substrate is 4-chloro-3,5-dinitro-benzotrifluoride.
7. A method according to claim 1 wherein said substrate is mixed with said chlorinating agent before it is vaporized.
8. A method according to claim 1 wherein said chlorinating agent is chlorine.
9. A method according to claim 1 wherein said mixture is reacted in a column packed with an inert material.
10. A method according to claim 1 wherein said substrate is selected from the group consisting of chloro-substituted benzotrifluorides, chloro-substituted benzoyl chlorides, chloro-substituted trifluoromethoxybenzenes, chloro-substituted pentafluoroethoxybenzenes, chloro-substituted benzonitriles, and chloro-substituted phenyl isocyanates.
11. A method according to claim 1 wherein said substrate and said partially reacted substrate are condensed in a column packed with an inert material.
12. A method according to claim 1 wherein the amount of said chlorinating agent is about 0.8 to about 1.4 times the amount needed to stoichiometrically replace the nitro groups on said substrate.
13. A method according to claim 1 wherein said vaporized mixture is heated to about 290 to about 350° C.
14. A method according to claim 1 wherein step (B) is performed in a reactor and steps (B), (C), and (D) are repeated until at least 95 wt % of the organic overhead from said reactor is said chlorinated aromatic compound.
15. A method of making a chlorinated aromatic compound having the general formula

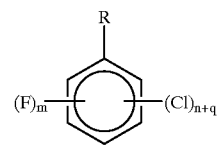

comprising
   (A) vaporizing a substrate having the general formula

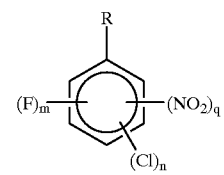

where R is $CF_3$, $OCF_3$, $OC_2F_5$, CN, NCO, or COCl, m is 0, 1, or 2, n is 0, 1, or 2, q is 1 or 2, q+m+n is an integer from 1 to 5;
   (B) preparing a mixture of said vaporized substrate and chlorine where the amount of chlorine in said mixture is about 0.8 to about 1.4 times the amount stoichiometrically required to replace the nitro groups on said substrate;
   (C) heating said vaporized mixture in a reactor to about 290 to about 350° C. to produce a product mixture;
   (D) condensing said substrate and partially reacted substrate from said product mixture;
   (E) recycling said condensed substrate and said condensed partially reacted substrate to step (A);
   (F) repeating steps (B), (C), (D) and (E) until at least 95 wt % of the organic overhead from said reactor is said chlorinated aromatic compound; and (G) isolating said chlorinated aromatic compound from said overhead.

16. A method according to claim 15 wherein said substrate is selected from the group consisting of chloro-substituted benzotrifluorides, chloro-substituted benzoyl chlorides, chloro-substituted trifluoromethoxybenzenes, chloro-substituted pentafluoroethoxybenzenes, chloro-substituted benzonitriles, and chloro-substituted phenyl isocyanates.

17. A method according to claim 15 wherein said substrate is 4-chloro-3,5-dinitro-benzotrifluoride.

18. A method of making 3,4,5-trichlorobenzotrifluoride comprising (A) preparing mixture of liquid 4-chloro-3,5-dinitrobenzotrifluoride and about 0.8 to about 1.4 moles of chlorine gas per mole of said liquid 4-chloro-3,5-dinitrobenzotrifluoride;

(B) vaporizing said liquid 4-chloro-3,5-dinitrobenzotrifluoride in said mixture;

(C) heating said mixture in a reactor to about 290 to about 350° C. to produce a product mixture;

(D) condensing aromatics that boil above about 180° C. from said product mixture;

(E) recycling said condensed aromatics to step (B):

(F) repeating steps (C), (D), and (E) until at least 95 wt % of the organic overhead from said reactor is 3,4,5-trichlorobenzotrifluoride; and (G) condensing said 3,4,5-trichlorobenzotrifluoride from said overhead.

19. A method according to claim 18 wherein said mixture is heated in a column packed with metallic nickel.

20. A method according to claim 18 wherein, in step (D), said aromatics are condensed in a column packed with metallic nickel.

* * * * *